Figure 1:
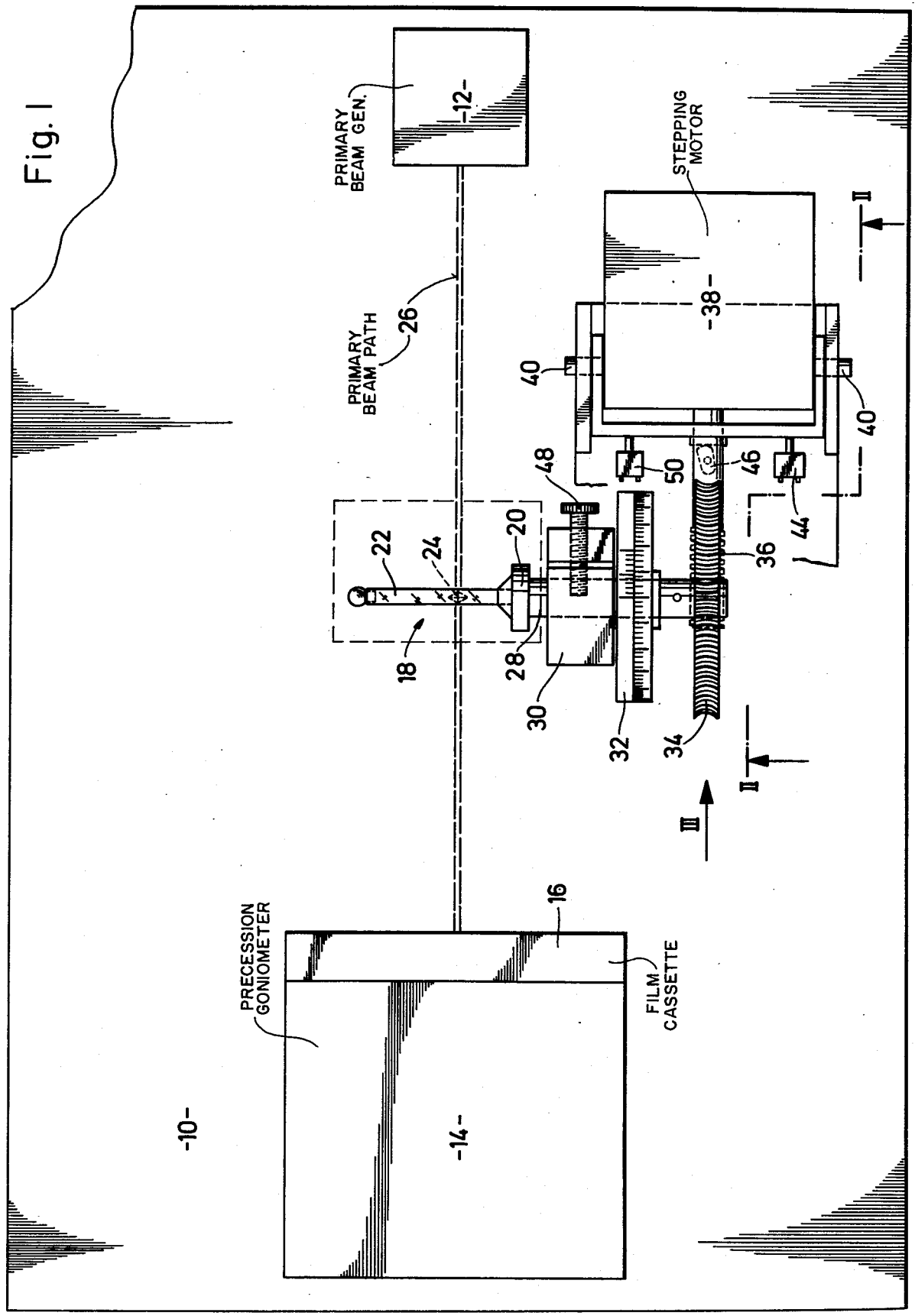

United States Patent

Steinbichler

[11] 4,071,758
[45] Jan. 31, 1978

[54] MULTIPLE TEST X-RAY GONIOMETER

[75] Inventor: Alfred Steinbichler, Munich, Germany

[73] Assignee: Max-Planck-Gesellschaft zur Förderung der Wissenschafter e.V., Gottingen, Germany

[21] Appl. No.: 710,301

[22] Filed: July 30, 1976

[30] Foreign Application Priority Data

Aug. 4, 1975   Germany ................ 2534790

[51] Int. Cl.² ........................................... G01M 23/20
[52] U.S. Cl. ............................. 250/277 CH; 250/451
[58] Field of Search ............... 250/277 CH, 272, 277, 250/446, 451

[56] References Cited

U.S. PATENT DOCUMENTS

| 3,189,741 | 6/1965 | Patser | 250/277 CH |
| 3,466,438 | 9/1969 | Abrahamsson | 250/277 CH |
| 3,566,112 | 2/1971 | Luecke | 250/277 CH |
| 3,631,240 | 12/1971 | Hoppe | 250/277 CH |
| 3,728,541 | 4/1973 | Rabinovich et al. | 250/277 CH |

Primary Examiner—Bruce C. Anderson
Attorney, Agent, or Firm—Flynn & Frishauf

[57] ABSTRACT

To permit X-ray analysis of crystals, selectively, with respect to both precession and rotation, without repositioning of the crystal and disturbance of crystal position, a goniometer head is located in the path of a primary X-ray beam and connected to a shaft which can be stepped in rotary movement by selective engagement through precision precession drive gearing. To prevent accidental engagement of the precession drive gearing, interlocks are provided to disable energization of the motor when rotation crystal diffraction tests are being made and the shaft is locked in position by a locking screw.

10 Claims, 3 Drawing Figures

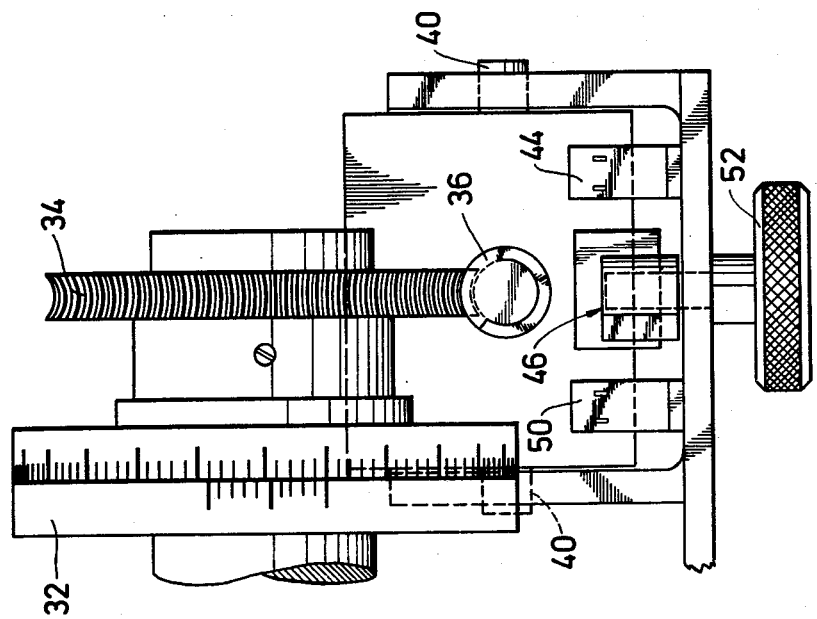
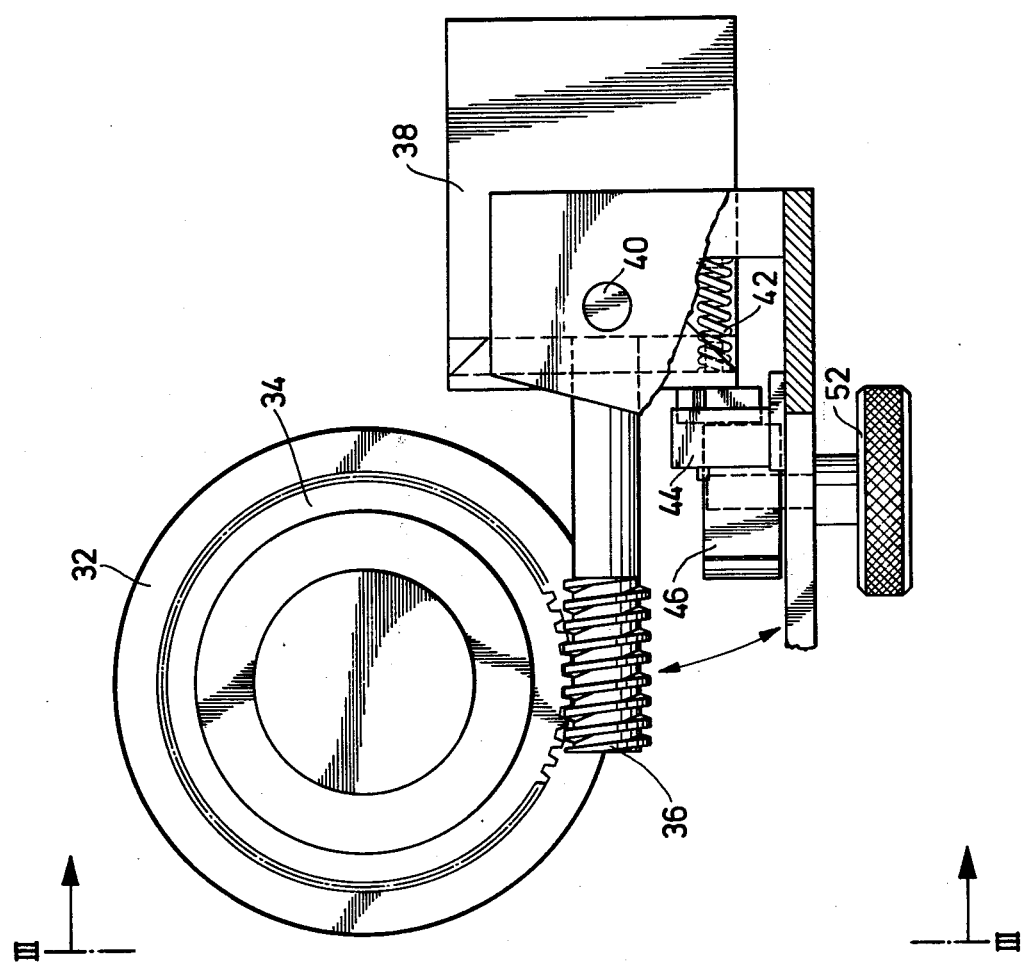

MULTIPLE TEST X-RAY GONIOMETER

The present invention relates to a multiple test X-ray goniometer, and more particularly to such an apparatus in which a goniometer head, holding a test crystal sample, is located in a primary X-ray beam and held on a shaft to permit representation of the reciprocal lattice of the crystal while, additionally, permitting structural analysis in accordance with the Bragg or rotation diffraction method.

Various types of apparatus have been proposed for X-ray analysis of crystal samples; for example, precession cameras are known and commercially available, as well as X-ray diffractometers, for example made by ENRAF NONIUS DELFT, and available commercially. It is well known in the art that X-ray analysis by means of a precession camera provides undistorted representation of the reciprocal lattice. In the diffractometer, the test sample is rotated when exposed to a monochromatic beam of X-rays in order to determine reflection angles.

Heretofore it has not been possible to utilize a single instrument for precession exposures as well as for rotary exposures. It was necessary to insert the crystal test sample first in one apparatus, then remove it and reinstall it in a different apparatus, each time requiring painstaking adjustment. This is time-consuming and difficult and, additionally, precise comparative test results are difficult to obtain.

It is an object of the present invention to provide an apparatus for X-ray analysis of crystals which permits exposures to be made both with respect to precession as well as with respect to rotation; and, more particularly, to provide an X-ray precession goniometer which, additionally, permits exposures in accordance with the rotation or diffraction test steps.

SUBJECT MATTER OF THE PRESENT INVENTION

Briefly, a goniometer head is located in the path of a primary X-ray beam and secured to a shaft which is coupled through a gearing to a motor, preferably to a stepping motor. The test sample is secured to the goniometer head. The drive gearing is so arranged that the driving connection between the motor and the shaft can be interrupted or broken, preferably by breaking the drive connection between gearing elements. In a preferred form, the gears include a worm gear of which one element can be rocked out of engagement with the other; when the shaft is thus out of engagement with the drive gear, it can be locked in precise position for precession testing. Interlocks are provided to prevent inadvertent engagement of the motor while the shaft is locked in position for such tests.

The apparatus, accordingly, permits exposures to be made both for precession as well as for rotation tests while having exactly the same conditions of the crystal with respect to the beam, thus eliminating multiple adjustment and permitting precise comparisons.

The invention will be described by way of example with reference to the accompanying drawings, wherein:

FIG. 1 is a highly schematic and simplified top view of an X-ray goniometer in accordance with the present invention, wherein standard components are shown in labelled blocks; and FIGS. 2 and 3 are fragmentary schematic side and end views, respectively, of the apparatus of FIG. 1.

A base plate 10 (FIG. 10) has mounted thereon a primary X-ray beam generator 12, a precession goniometer camera unit 14 having a film cassette or other suitable means to hold a film or sensing element, and a goniometer head unit 18. The primary beam generator 12, the precession unit 14 and the film holder 16 can all be parts of a commercially available precession camera and are therefore shown only in block form.

The goniometer head unit 18 includes the usual goniometer head 20 to which a glass capillary 22 is secured in which a test sample 24 in form of a crystal is included. The crystal is located within the path 26 of the primary beam. The goniometer head 20 is secured to a shaft 28 which is journalled in bearing 30. A scale 32 is connected to shaft 28 so that the angular position of the shaft can be manually adjusted to adjust the crystal position about its K-axis.

In accordance with the present invention, a gearing is additionally connected to shaft 28 and, in accordance with a feature thereof, includes a worm wheel 34 which is connectable with a worm 36 which, in turn, is connected to the drive shaft of a stepping motor 38 (see also FIGS. 2, 3). Assuming 200 steps for each rotation of the motor shaft, and suitable dimensioning of the worm gear 34, 36, a stepping angle of 0.01° of shaft 28 can be obtained.

Stepping motor 38, and the worm 36 secured to its shaft, is located for pivoting movement about axis 40—40 (see particularly FIG. 2) to rock thereabout. Springs 42 (FIG. 2) press the motor and hence the worm 36 in a position in which the worm 36 is in engagement with the worm wheel 34. A microswitch 44 is located on the frame or base plate 10 and so adjusted with respect to the motor 38, or one of its moving components, that the motor or drive means included in the precession camera is disabled when the gears 34, 36 of the stepping drive are engaged, so that the precession camera and its film cassette cannot be moved when the shaft 28 is coupled to the stepping motor 38.

The worm gear 34, 36 is rocked about axis 40 by an eccenter 46. Eccenter 46 operates in the manner of a cam to rock motor 38 and with it the worm 36 about the axis 40. When the motor is rocked about axis 40 to disengage the gearing, the microswitch 44 is closed and the precession unit can be operated.

The goniometer head can be set to a predetermined angular position suitable for precession measurements, and in order to prevent inadvertent shifting, a locking screw 48 (FIG. 1) is provided. Locking screw 48 is interlocked with a second microswitch 50, as schematically shown by the broken line connection. Microswitch 50 is included in the circuit of the motor 38 and so connected that the motor circuit for motor 38 can be closed only if the locking screw 48 is released. Thus, it is not possible to energize the stepping motor 38 when the locking screw 48 is locked, so that damage of the stepping motor or the gearing thereof is not possible.

One or both of the microswitches can additionally be simply connected to indicator lights in order to indicate which type of test is in progress-precession testing or rotation, that is, diffraction testing.

Operation: To make rotational exposures, the precession drive is placed in zero or null position, the locking screw 48 is released and the gear 34, 36 is engaged by suitable adjustment of the eccenter 46, by means of a handle knob 52 (FIGS. 2, 3). After placement and adjustment of the test sample 24, primary beam 12 is energized and the stepping motor can then be controlled in accordance therewith, so that the film material within the cassette holder 16 can be exposed.

To make precession exposures, the drive connection formed by gearing 34, 36 is broken by suitable movement of the eccenter or cam 46 by operating the handle knob 52. The goniometer shaft 28 is then placed in a suitable test position, as measured on scale 32 (FIG. 1) and locked in position by means of locking screw 48. Precession exposures can then be made as well known and in accordance with customary procedures.

The X-ray goniometer, therefore, can be used to make various tests on a single sample without repetitive placement in different apparatus, without loss of time and permitting making of precession exposures as well as rotary angle exposures without changing the sample with respect to the primary beam, thus ensuring identical conditions for both types of tests and permitting accurate comparison of the resulting data.

Various changes and modifications may be made within the scope of the inventive concept.

I claim:

1. Multiple test X-ray goniometer for X-ray analysis of crystals, selectively, with respect to precession and rotation, without disturbance of crystal position with respect to an X-ray beam, comprising
   a precession camera unit (14)
   a goniometer head (18) located in the path (26) of a primary beam and having means (22) to hold a crystal test sample (24) in a predetermined position relative to said precession camera;
   a shaft (28) rotatably supporting said goniometer head (18) and hence said crystal test sample (24);
   a drive gearing (34, 36) coupled to the shaft (28) to rotate the shaft and hence the goniometer head (18), and with it the crystal test sample (24) in the holding means (22);
   motor drive means (38) coupled to the drive gearing (34, 36), the drive gearing (34, 36) and the shaft forming a drive train for the goniometer head (18);
   locking means (48) engageable with the shaft (28) of the goniometer head (20) to fix the goniometer head shaft (28) and hence the crystal test sample (24) in position;
   and wherein the drive continuity of said drive train is selectively interruptable to interrupt transmission of rotary movement between said shaft (28) of the goniometer head (20) and the drive motor (38) and prevent application of drive power to said shaft when the locking means have engaged the shaft to fix it in position.

2. X-ray goniometer according to claim 1, wherein the drive motor (38) is a stepping motor.

3. X-ray goniometer according to claim 1, wherein the drive gearing comprises meshing gear means (34, 32) which are selectively disengageable.

4. X-ray goniometer according to claim 3, wherein the drive gearing comprises a worm (36) coupled to the drive motor (38), a worm wheel (34) coupled to the goniometer head shaft (28), the worm (36) being pivotable along its axis for selective disengagement with the worm wheel (34).

5. X-ray goniometer according to claim 4, further comprising spring bias means (42) providing a spring bias force to the worm (36) and tending to engage the worm (36) with the worm wheel (34);
   and manual operating means (46, 52) engageable with the worm (36) to move the worm counter the spring force and out of engagement with the worm wheel (34).

6. X-ray goniometer according to claim 5, wherein the manual operating means comprises an eccentric cam disk (46), and manual means rotating the cam disk to cam the motor and with it the worm (36), selectively, into and out of engagement with the worm gear (34).

7. X-ray goniometer according to claim 1, further comprising;
   stop interlock means (50) electrically connected to the drive motor (38) to disable energization of the drive motor when the locking means (48) are in position to lock the shaft (28).

8. X-ray goniometer according to claim 1, further comprising safety interlock means (44) electrically connected to the precession camera unit (14) and operable conjointly with interruption of the interruptable transmission and preventing movement of said precession camera unit (14) when the drive gears (34, 36) are coupled to transmit rotation to said shaft (28).

9. X-ray goniometer according to claim 1, further comprising
   stop interlock means (50) electrically connected to the drive motor (38) to disable energization of the drive motor when the locking means 48 are in position to lock the shaft (28);
   and safety interlock means (44) electrically connected to the precession camera unit (14) and operable conjointly with interruption of the interruptable transmission and preventing movement of said precession camera unit (14) when the drive gears (34, 36) are coupled to transmit rotation to said shaft (28).

10. X-ray goniometer according to claim 9, wherein the drive train includes a worm (36) coupled to the drive motor (38), a worm wheel (34) coupled to the goniometer head shaft (28), the worm (36) being pivotable along its axis for selective engagement or disengagement with the worm wheel (34);
    spring bias means (42) providing a spring bias force to the worm (36) and tending to engage the worm (36) with the worm wheel (34);
    and manual operating means (46, 52) engageable with the worm (36) to move the worm counter the spring force and out of engagement with the worm wheel (34).

* * * * *